United States Patent
Jenusaitis et al.

(10) Patent No.: US 6,562,062 B2
(45) Date of Patent: May 13, 2003

(54) BALLOON ANCHORING SYSTEM

(75) Inventors: Matthew Jenusaitis, San Diego, CA (US); Paul LaViolette, Wellesley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/927,135

(22) Filed: Aug. 10, 2001

(65) Prior Publication Data

US 2003/0032973 A1 Feb. 13, 2003

(51) Int. Cl.[7] .................................................. A61F 2/06
(52) U.S. Cl. ...................................... 623/1.11; 606/194
(58) Field of Search ............................ 623/1.11, 1.12, 623/1.13, 1.14, 1.15, 1.16, 1.17, 1.18, 1.19, 1.2; 606/159, 191, 194, 198, 195, 192; 604/96–101, 103

(56) References Cited

U.S. PATENT DOCUMENTS

| | | | |
|---|---|---|---|
| 4,273,128 A | 6/1981 | Lary | |
| 4,307,722 A | 12/1981 | Evans | |
| 4,793,348 A | 12/1988 | Palmaz | |
| 4,921,483 A | 5/1990 | Wijay | |
| 4,921,484 A | 5/1990 | Hillstead | |
| 5,009,659 A | 4/1991 | Hamlin | |
| 5,176,693 A | 1/1993 | Pannek, Jr. | |
| 5,196,024 A | 3/1993 | Barath | |
| 5,320,634 A | * 6/1994 | Vigil et al. | 604/103.08 |
| 5,336,234 A | * 8/1994 | Vigil et al. | 604/103.08 |
| 5,797,935 A | * 8/1998 | Barath | 606/159 |
| 5,807,326 A | * 9/1998 | O'Neill et al. | 604/103.04 |
| 2002/0010489 A1 | * 1/2002 | Grayzel et al. | 606/194 |

* cited by examiner

Primary Examiner—Michael J. Milano
Assistant Examiner—Vy Q. Bui
(74) Attorney, Agent, or Firm—Nydegger & Associates

(57) ABSTRACT

A system for anchoring an angioplasty catheter to a stenosis in the vasculature of a patient includes an elongated inflatable balloon that can be selectively moved between a deflated configuration and an inflated configuration. Optionally, the system can include a stent mounted on the balloon. The balloon defines an axis and has at least one elongated blade which is axially oriented on the surface of the balloon. Also this blade is conformed with at least one azimuthally oriented grip. When the balloon is moved into its inflated configuration, to thereby embed the blade and its grip into the stenosis and expand the stent for emplacement in the vasculature, the axially oriented blade prevents an azimuthal movement of the balloon and the azimuthally oriented grip prevents an axial movement of the balloon relative to the stenosis.

16 Claims, 2 Drawing Sheets

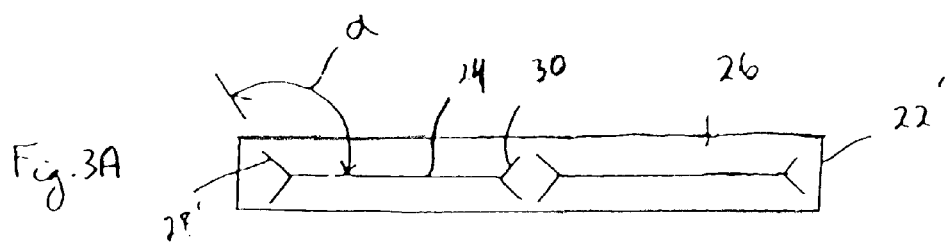
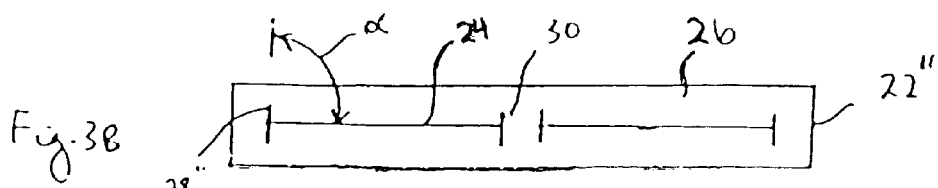
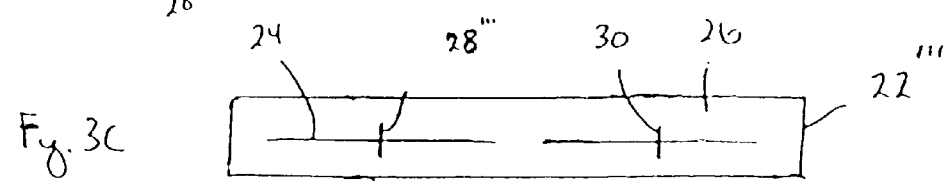
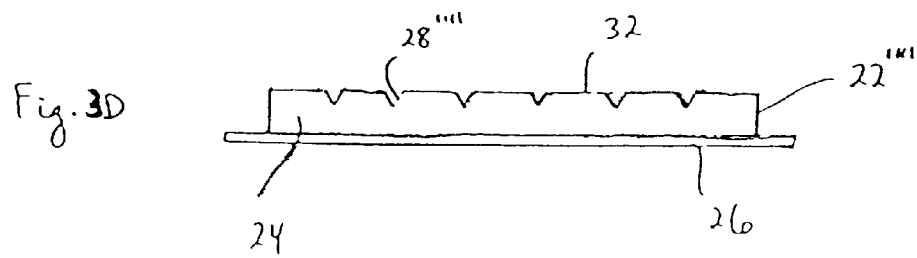
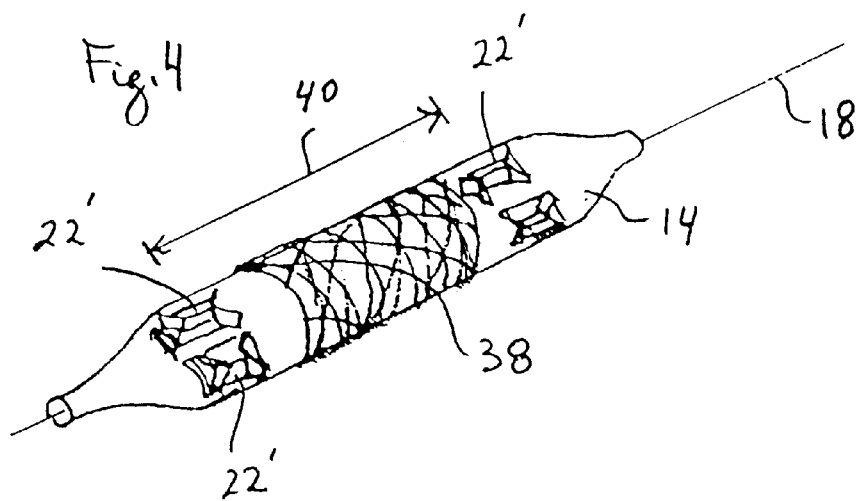

BALLOON ANCHORING SYSTEM

FIELD OF THE INVENTION

The present invention pertains generally to devices and methods for performing angioplasty or stent emplacement procedures. More particularly, the present invention pertains to angioplasty balloon catheters that incorporate cutting blades on the surface of the balloon. The present invention is particularly but not exclusively useful as a device and method which incorporates a cutting blade that will anchor the balloon to the stenosis during an angioplasty procedure or the emplacement of a stent in the vasculature of a patient.

BACKGROUND OF THE INVENTION

Angioplasty and stent emplacement procedures have been successfully used for many years for the treatment of vasculature diseases. Typically, in an angioplasty procedure, an inflatable balloon is inserted on a catheter into the vasculature and is positioned in a vessel of the vasculature at the site of a stenosis. The balloon is then inflated to dilate the stenosis for improved blood flow through the vessel. Inflatable balloons are also widely used for procedures wherein a stent is to be positioned into the vasculature of a patient.

In recent years a significantly important advancement has been made in angioplasty procedures with the introduction of the so-called "cutting balloon." More specifically, such a "cutting balloon" incorporates blades which are mounted on the surface of the balloon to cut into a stenosis as the balloon is inflated to dilate the stenosis. For example, such a "cutting balloon" is disclosed and claimed in U.S. Pat. No. 5,797,935 which issued to Barath for an invention entitled "Balloon Activated Force Concentrators for Incising Stenotic Segments" and which is assigned to the same assignee as the present invention. It happens, however, that despite such significant technical advances, the very nature of a particular stenosis can pose additional concerns for consideration.

As is well known, a stenosis in a vessel of the vasculature can be one of many different types and can have various configurations. For instance, some are of a rather slippery consistency. Additionally they may have a configuration that makes it particularly difficult to maintain the position of an angioplasty balloon at the site of the stenosis as the balloon is being inflated. Specifically, it can happen that as the balloon is being inflated, the forces that are generated between the balloon and the stenosis can cause the balloon to be displaced from the site of the stenosis. Obviously, this so-called "watermelon seed" reaction can be disruptive of an angioplasty procedure.

The above-noted problems are also present, and can be particularly troublesome, in procedures wherein a stent is to be emplaced at a site in the vasculature. As mentioned above, such sites may involve a slippery stenosis that can adversely effect efforts to properly position the stent.

In light of the above, it is an object of the present invention to provide a system and method for anchoring the inflatable balloon of a balloon catheter to a stenosis in the vasculature of a patient during an angioplasty or stent emplacement procedure. Another object of the present invention is to provide an improved "cutting balloon" catheter which incorporates specifically configured blades that will prevent both axial (translational) and azimuthal (rotational) movements of the balloon relative to the vessel (stenosis site) during an angioplasty procedure. Still another object of the present invention is to provide a system and method for anchoring the balloon of an angioplasty balloon catheter to a stenosis in the vasculature of a patient that is relatively simple to manufacture, is easy to implement, and is comparatively cost effective.

SUMMARY OF THE PREFERRED EMBODIMENTS

A system and method for anchoring an angioplasty catheter to a stenosis in the vasculature of a patient requires an elongated inflatable balloon and specially configured blades mounted on the surface of the balloon. More specifically, the balloon defines a longitudinal axis and is mounted on a catheter for selective movement between a deflated configuration and an inflated configuration. In the deflated configuration the surface of the balloon is effectively collapsed onto the axis. In the inflated configuration, however, the surface of the balloon is radially distanced from the axis.

For the present invention, at least one elongated blade (main-blade) is mounted on the surface of the balloon. Preferably, the main-blade is axially oriented substantially parallel to the axis that is defined by the balloon. Additionally, there is at least one grip that is conformed with the blade. More specifically, the grip is azimuthally oriented on the axis that is defined by the balloon, and it protrudes in a substantially radial direction from the axis of the balloon.

For one embodiment of the present invention the grip is a serration(s) that is formed into the cutting edge of the main-blade. In another embodiment the grip is a cross-blade that forms an angle α with the blade. In accordance with the present invention this angle α can be ninety degrees, or it may be greater or less than ninety degrees depending on the particular needs of the user. Further, as contemplated for the present invention, the blade and the grip can be made of stainless steel.

For an alternate embodiment of the present invention the system can include a stent that is to be emplaced in the vasculature of the patient. Specifically, as is well known, the stent is positioned on the balloon for movement with the balloon as the balloon is inflated from its deflated configuration and into its inflated configuration. Thus, the stent can be expanded for emplacement in the vasculature of the patient. Further, when a stent is included in the system of the present invention there can be a plurality of anchoring blades mounted on the balloon. In this case, preferably, each blade is axially aligned with at least one other blade, with a distance therebetween. The stent can then be positioned on the balloon between the blades.

In operation, as the balloon is inflated into its inflated configuration, the blade and its conformed grip are embedded into the stenosis. This effectively anchors the balloon to the stenosis as the axially oriented main-blade prevents azimuthal (rotational) movement in the vessel relative to said stenosis. At the same time the azimuthally oriented grip prevents axial (translational) movement of the balloon in the vessel relative to the stenosis.

It is within the contemplation of the present invention that the system will include a plurality of main-blades. Furthermore, it is contemplated that each of the plurality of main-blades may have a plurality of conformed grips. Additionally, some of the plurality of main-blades can be axially aligned with each other. Also, each main-blade can be azimuthally distanced from at least one other main-blade by an angle β. Thus, a series of main-blades can be present in different azimuthal locations on the surface of the balloon.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is a top plan view of a blade and grip arrangement in accordance with the present invention;

FIG. 3B is a top plan view of an alternative blade and grip arrangement in accordance with the present invention;

FIG. 3C is a top plan view of yet another alternative blade and grip arrangement in accordance with the present invention;

FIG. 3D is a side elevation view of yet another embodiment of a blade and grip arrangement that is useful for the present invention; and FIG. 4 is a perspective view of an alternate embodiment of the present invention showing the incorporation of a stent.

DESCRIPTION OF THE PREFERRED EMBODIMENT

Figure 1:
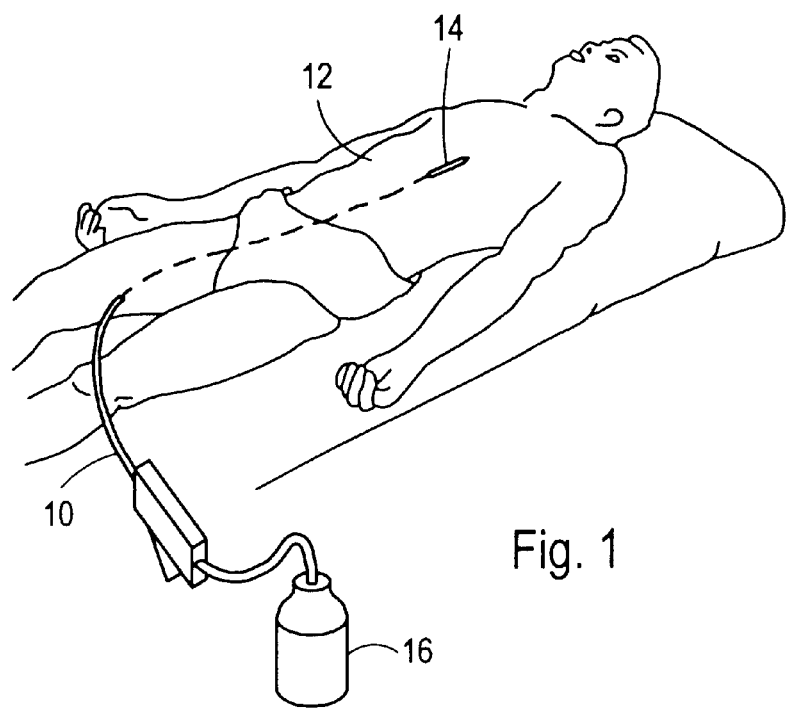
FIG. 1 is a perspective view of a patient undergoing an angioplasty procedure with a balloon catheter that incorporates the present invention.

Referring initially to FIG. 1, a balloon catheter in accordance with the present invention is shown and designated 10. As shown in FIG. 1, the balloon catheter 10 is positioned in the vasculature of a patient 12 for the purpose of performing an angioplasty procedure. To do this, the balloon catheter 10 includes an inflatable balloon 14 and an inflation pump 16 that is connected in fluid communication with the balloon 14. More specifically, activation of the pump 16 by a user causes the balloon 14 to be selectively moved between a deflated configuration and an inflated configuration.

Figure 2:
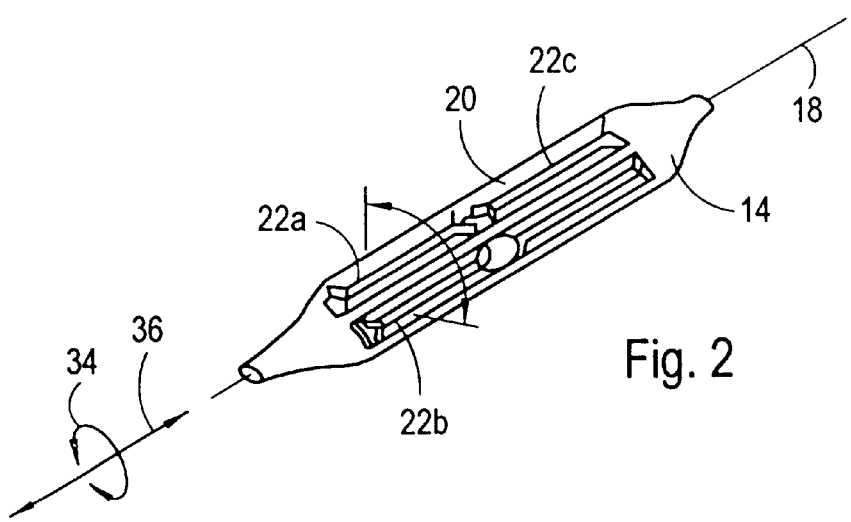
FIG. 2 is a perspective view of a preferred embodiment of the present invention.

In more detail, FIG. 2 shows the balloon 14 in its inflated configuration. In this configuration it can be seen that the balloon 14 of the present invention, like typical angioplasty balloons, is elongated and generally defines an axis 18 that extends the length of the balloon 14. The balloon 14 also has a surface 20 on which a plurality of elongated blade elements 22 can be mounted. In accordance with the present invention, the orientation of the blade elements 22 on the surface 20 of balloon 14, and the characteristics of the individual blade elements 22 can be varied to meet the particular requirements and specifications of the user. The blade elements 22a, 22b and 22c shown in FIG. 2 are only exemplary.

For the purposes of the present invention, it is preferable that each blade element 22, when mounted on the surface 20 of balloon 14, be oriented substantially parallel to the axis 18. Further, as shown in FIG. 2, a plurality of the blade elements 22 can be axially aligned with each other (e.g. blade elements 22a and 22c). Also, the blade elements 22 can be azimuthally distanced from one another (e.g. blade elements 22a and 22b). In particular, the blade elements 22 can be azimuthally distanced from one another by an angle $\beta$ which will preferably position the blade elements 22 uniformly around the axis 18. For example, the angle $\beta$ may be ninety degrees, one hundred twenty degrees, or one hundred eighty degrees.

Variations in the characteristics of the blade elements 22 will be best appreciated with reference to FIGS. 3A, 3B, 3C, and FIG. 3D. In all instances, each blade element 22 preferably includes an elongated main-blade 24 which can be axially oriented on the surface 20. Also, each blade element 22 is mounted on a base member 26 which, in turn, can be mounted on the surface 20 of the balloon 14 in a manner well known in the art, such as by bonding. Thus, all blade elements 22 have several common characteristics. The significant characteristic difference between the various embodiments of the blade elements 22, however, is in the respective grips 28 that are conformed with the main-blade 24.

For one embodiment of the present invention, a blade element $22^1$ has a main-blade 24 that is conformed with a grip $28^1$. More specifically, as shown in FIG. 3A, the grip $28^1$ includes a cross-blade 30 that is oriented at an angle $\alpha$ relative to the main-blade 24. The angle $\alpha$ may vary and may be either greater than or less than ninety degrees. Specifically, for the grip $28^1$ shown in FIG. 3A, the angle $\alpha$ is greater than ninety degrees. For the grip $28^{11}$ of the blade element $22^{11}$ shown in FIG. 3B, however, the angle $\alpha$ between the main-blade 24 and the cross-blade 30 is substantially equal to ninety degrees. Also, as shown in both FIGS. 3A and 3B, the main-blade 24 of blade elements $22^1$ or $22^{11}$ can be conformed with a respective grip $28^1$ or $28^{11}$ at each end of the main-blade 24. Alternatively, a single cross-blade 30 can be positioned substantially midway between the ends of the main-blade 24 as shown in FIG. 3C for the grip $28^{111}$ of a blade element $22^{111}$. In yet another variation, the blade element $22^{1111}$ shown in FIG. 3D has a main-blade 24 which is formed with a grip $28^{1111}$ that includes at least one serration along the cutting edge 32 of the main-blade 24.

For the embodiments of the blade elements $22^1$, $22^{11}$, $22^{111}$ and $22^{1111}$ discussed above, all of the respective grips 28 have the common characteristic that they protrude outwardly from the surface 20 of the balloon 14 in a generally radial direction from the axis 18. Furthermore, as they radially protrude from the axis 18, all of the grips 28 present an azimuthally oriented exterior. Preferably, the grips 28 and main-blades 24 are all made of stainless steel.

In the operation of the balloon catheter 10 of the present invention, the balloon 14 is initially deflated so that its surface 20 is collapsed onto the axis 18. The balloon catheter 10, in its deflated configuration, is then inserted into the vasculature of the patient 12 to position the balloon 14 at the site of a stenosis (not shown). The balloon 14 is then inflated using the inflation pump 16. This causes the surface 20 of the balloon 14 to be radially distanced from the axis 18 to thereby dilate the stenosis and embed the blade element(s) 22 into the stenosis. After the stenosis has been dilated, the balloon 14 is deflated and the balloon catheter 10 is removed from the vasculature of the patient 12.

Important aspects of the present invention are that while the blade element(s) 22 are embedded into the stenosis during an angioplasty procedure, the balloon 14 is effectively held at the site of the stenosis. Specifically, the balloon 14 is prevented from moving either azimuthally in rotation (in the directions of arrows 34, shown in FIG. 2), or axially in translation (in the directions of arrows 36 (also shown in FIG. 2). More specifically, when the balloon 14 is inflated at the site of the stenosis, azimuthal (rotational) constraints are imposed on the balloon 14 by the axially oriented main-blades 24 of the blade element 22. At the same time, axial (translational) constraints are imposed on the balloon 14 by azimuthally oriented components of the grip(s) 28. Thus, the grip(s) 28, having cross-blades 30 (FIGS. 3A, 38 and 3C) or serrations in cutting edge 32 (FIG. 3D), in combination with the main-blades 24, hold the balloon 14 at the site of a stenosis during an angioplasty procedure. Importantly, this effectively prevents the so-called "watermelon seed" effect noted above.

For an alternate embodiment of the present invention, as shown in FIG. 4, a stent 38, of any type well known in the pertinent art, can be mounted on the balloon 14. For purposes of the present invention, the stent 38 needs to be expandable as the balloon 14 is inflated, and the stent 38 should be positioned on the balloon 14 so that the blade elements $22^1$ can function as disclosed above. Although FIG. 4 shows the use of a plurality of blade elements $22^1$, it is to be appreciated that as few as one blade element $22^1$ can be used. When a plurality of blade elements $22^1$ are used, however, it is preferable that each blade element $22^1$ be axially aligned with another blade element $22^1$, and that the aligned blade elements $22^1$ be separated from each other by a distance 40. Specifically, as shown in FIG. 4, the distance 40 is established to provide for the positioning of the stent 38 on the balloon.

While the particular Balloon Anchoring System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for anchoring an angioplasty catheter to a stenosis in the vasculature of a patient which comprises:
    an elongated inflatable balloon having a surface and defining a longitudinal axis, said balloon being mounted on said catheter for selective movement between a deflated configuration wherein said surface of said balloon is collapsed on said axis, and an inflated configuration wherein said surface is radially distanced from said axis;
    at least one elongated blade mounted on said surface of said balloon substantially parallel to said axis of said balloon;
    at least one azimuthally oriented cross-blade grip conformed with said blade, said grip being oriented to protrude in a substantially radial direction from said axis; and
    a means for inflating said balloon into said inflated configuration to embed said blade and said grip into said stenosis to anchor said balloon thereto by respectively preventing azimuthal and axial movements of said balloon relative to said stenosis.

2. A system as recited in claim 1 further comprising a stent positioned on said balloon for movement therewith from said deflated configuration into said inflated configuration to expand said stent for emplacement in the vasculature of the patient.

3. A system as recited in claim 2 further comprising a plurality of said blades, with each said blade axially aligned with at least one other said blade, and with a distance therebetween for positioning said stent therebetween on said balloon.

4. A system as recited in claim 1 wherein said grip is a serration formed on said blade.

5. A system as recited in claim 1 wherein said cross-blade grip forms an angle α with said blade.

6. A system as recited in claim 5 wherein said angle α is ninety degrees.

7. A system as recited in claim 5 wherein said angle α is greater than ninety degrees.

8. A system as recited in claim 1 wherein said blade and said grip are made of stainless steel.

9. A system as recited in claim 1 wherein there are a plurality of said blades, and further wherein each said blade has a plurality of conformed grips.

10. A system as recited in claim 1 wherein a plurality of said blades are axially aligned with each other.

11. A system as recited in claim 1 wherein there are a plurality of said blades, and further wherein each said blade is azimuthally distanced from at least one other said blade by an angle β.

12. A method for anchoring an angioplasty catheter to a stenosis in the vasculature of a patient which comprises the steps of:
    providing an elongated inflatable balloon having a surface and defining a longitudinal axis, said balloon being mounted on said catheter for selective movement between a deflated configuration wherein said surface of said balloon is collapsed on said axis, and an inflated configuration wherein said surface is radially distanced from said axis, with at least one elongated blade mounted on said surface of said balloon substantially parallel to said axis of said balloon, and at least one azimuthally oriented cross-blade grip conformed with said blade, said grip being oriented to protrude in a substantially radial direction from said axis;
    inserting said balloon to the site of the stenosis in the vasculature; and
    inflating said balloon into said inflated configuration to embed said blade and said grip into said stenosis to anchor said balloon thereto by respectively preventing azimuthal and axial movements of said balloon relative to said stenosis.

13. A method as recited in claim 12 further comprising the step of mounting a stent on said balloon for movement therewith from said deflated configuration to said inflated configuration for emplacement of said stent into the vasculature of the patient.

14. A method as recited in claim 12 wherein said grip is a serration formed on said blade.

15. A method as recited in claim 12 wherein said cross-blade grip forms an angle α with said blade.

16. A system for anchoring an angioplasty catheter to a stenosis in the vasculature of a patient which comprises:
    an elongated inflatable balloon having a surface and defining a longitudinal axis, said balloon being mounted on said catheter for selective movement between a deflated configuration wherein said surface of said balloon is collapsed on said axis, and an inflated configuration wherein said surface is radially distanced from said axis;
    at least one elongated blade mounted on said surface of said balloon substantially parallel to said axis of said balloon;
    at least one grip conformed with said blade, said grip being oriented to protrude in a substantially radial direction from said axis;
    a means for inflating said balloon into said inflated configuration to embed said blade and said grip into said stenosis to anchor said balloon thereto by respectively preventing azimuthal and axial movements of said balloon relative to said stenosis; and
    a stent positioned on said balloon for movement therewith from said deflated configuration into said inflated configuration to expand said stent for emplacement in the vasculature of the patient.

* * * * *

UNITED STATES PATENT AND TRADEMARK OFFICE
CERTIFICATE OF CORRECTION

PATENT NO.     : 6,562,062 B2
DATED          : May 13, 2003
INVENTOR(S)    : Matthew Jenusaitis and Paul LaViolette It is certified that error appears in the above-identified patent and that said Letters Patent is hereby corrected as shown below:

<u>Column 4,</u>
Line 62, delete "38" insert -- 3B --

<u>Column 5,</u>
Line 35, after the word "blade" and before the word "mounted" insert -- with a sharp cutting edge --
Line 38, after the word "grip" and before the word "conformed" insert -- with a sharp cutting edge --

<u>Column 6,</u>
Line 19, after the word "blade" insert -- with a sharp cutting edge --
Lines 22 and 54, after the word "grip" and before the word "conformed" insert -- with a sharp cutting edge --
Line 51, afte the word "blade" and before the word "mounted" insert -- with a sharp cutting edge --
Line 54, after the word "one" and before the word "grip" insert -- azimuthally oriented cross-blade --

Signed and Sealed this

Second Day of September, 2003

JAMES E. ROGAN
*Director of the United States Patent and Trademark Office*